United States Patent
Raz et al.

(10) Patent No.: US 6,514,948 B1
(45) Date of Patent: *Feb. 4, 2003

(54) METHOD FOR ENHANCING AN IMMUNE RESPONSE

(75) Inventors: Eyal R. Raz, Del Mar, CA (US); Hiroko Kobayashi, Fukushima (JP)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/347,343

(22) Filed: Jul. 2, 1999

(51) Int. Cl.$^7$ .................. A61K 31/70; C07H 21/04; C12N 15/63

(52) U.S. Cl. .................. 514/44; 536/23.1; 536/24.1; 536/24.5; 435/320.1

(58) Field of Search .................. 424/184.1, 234.1, 424/278.1, 282.1; 514/44; 536/23.1, 24.1, 24.5; 435/69.1, 320.1, 325, 455, 459

(56) References Cited

U.S. PATENT DOCUMENTS

| | | | |
|---|---|---|---|
| 5,679,647 A | 10/1997 | Carson et al. | 514/44 |
| 5,736,524 A | 4/1998 | Content et al. | 514/44 |
| 5,780,448 A | 7/1998 | Davis | 514/44 |
| 5,849,719 A | 12/1998 | Carson et al. | 514/44 |
| 6,194,388 B1 | 2/2001 | Krieg et al. | 514/44 |
| 6,207,646 B1 | 3/2001 | Krieg et al. | 514/44 |

FOREIGN PATENT DOCUMENTS

| WO | WO 98/16247 | 4/1998 |
|---|---|---|
| WO | WO 99/11275 | 3/1999 |

OTHER PUBLICATIONS

Threadgill et al. Vaccine. 16(1):76–82, 1998.*
Ott et al. MF59, Chapter 10, Vaccine Design: The Subunit and Adjuvant Approach, Plenum Press, NY, 1995.*
Elkins, et al., "Bacterial DNA Containing CpG Motifs Stimulates Lymphocytes–Dependent Protection if Mice Against Lethal Infection with Intracellular Bacteria," *The Journal of Immunology*, (Feb. 1999) 162:2291–2298.
Kreig, et al., "CpG DNA Induces Sustained IL–12 Expression In Vivo and Resistance to Listeria monocytogenes Challenge," *The Journal of Immunology*, (1998) 161:2428–2434.
Oxenius, et al., "CpG–Containing Oligonucleotides Are Efficient Adjuvants for Induction of Protective Antiviral Immune Responses with T–Cell Peptide Vaccines," *Journal of Virology*, (May 1999) 73(5):4120–4126.

Martin–Orozco, E. et al. "Enhancement of antigen–presenting cell surface molecules involved in cognate interactions by immunostimulatory DNA sequences." *International Immunology*, Mar. 1999, vol. 11 No. 7. pp. 1111–1118.
Kobayashi, et al., "Immunostimulatory DNA Prpeiming: A Novel Approach for Prolonged Th–1 biased Immunity," *Cellular Immunology* (Nov. 25, 1999) 198(1):69–75.
Spiegleberg, et al., "Inhibition of Allergic Inflammation in the Lung by Plasmid DNA Allergen Immunization," *Pediatric Pulmonology* (1999) 18:118–121.
David Broide et al., "Immunostimulatory DNA Sequences Inhibit IL–5, Eosinophilic Inflammation, and Airway Hypterresponsiveness in Mice", *The Journal of Immunology*, 1998, pp. 7054–7062.
David Broide et al, DNA–Based Immunization for Asthma, *Int'l. Archives of Allergy and Immunology*, 1999: 118:453–456.
Anthony A. Horner et al., "Rapid Communication: Immunostimulatory DNA is a Potent Mucosal Adjuvant", *Cellular Immunology*, 1998: 190:77–82 (Article No. CI981400).
Arthur M. Krieg et al., "CpG Motifs in Baterial DNA Trigger Direct B–Cell Activation", *Letters to Nature*, Apr. 6, 1995, vol. 374, Issue No. 6522, 546–549.

(List continued on next page.)

*Primary Examiner*—Anne M. Wehbe
*Assistant Examiner*—Janice Li
(74) *Attorney, Agent, or Firm*—Paula A. Borden; Carol L. Francis; Bozicevic Field & Francis, LLP

(57) ABSTRACT

Disclosed is a method for enhancing an immune response to a substance, such as an antigen or microbial pathogen. The immune response can be, for example, production of IgG2 antibodies. The method comprises administering an immunostimulatory nucleotide sequence (ISS) to a subject at least one hour prior to exposure to the substance by the subject. The subject may be exposed to the substance either naturally, as with an environmental pathogen, or by administration, as with a known antigen. The method can be used for protecting or immunizing a subject against an antigen or pathogen, providing more effective immunization than if the ISS were co-administered with the substance. The method can be used prophylactically or therapeutically. In preferred embodiments, the ISS comprises a CG, p(GC) or p(IC) DNA or RNA nucleotide sequence. Of these, a CG containing nucleotide sequence is preferred. The ISS can further comprise a pG nucleotide sequence. Examples of an ISS include sequences comprising 5'-rrcgyy-3', 5'-rycgyy-3', 5'-rrcgyycg-3' or 5'-rycgyycg-3'. The ISS is preferably administered between about 6 hours and about 6 weeks prior to exposure to the substance, and more preferably between about 1 day and about 4 weeks prior. Most preferably, the ISS is administered between about 3 days and about 8 days prior to exposure to the substance. The ISS can be administered via a mucosal or systemic route. The substance can be an antigen or pathogen associated with an infectious disease, an allergen or a cancer.

14 Claims, 5 Drawing Sheets

OTHER PUBLICATIONS

Dennis Klinman et al., "Contribution of CpG Motifs to the Immunogenicity of DNA Vaccines", *Journal of Immunology*, Apr. 15, 1997, 158(8):3635–3639.

Claude Leclerc et al., "The Preferential Induction of a Th1 Immune Response by DNA–based Immunization is Mediated by the Immunostimulatory Effect of Plasmid DNA", *Cell Immunol.*, Aug. 1, 1997, 179(2):97–106.

H.X. Lin et al., "A New Immunostimulatory Complex (PICKCa) in Experimental Rabies: Antiviral and Adjuvant Effects", *Archives of Virology*, 1993, 131: 307–319.

Mark Roman et al., "Immunostimulatory DNA Sequences Function as T Helper–1–Promoting Adjuvants", *Nature Medicine*, Aug. 1997:3:(8): 849–854.

H.L. Spiegelberg et al., "Inhibition of IgE Formation and Allergic Inflammation by Allergen Gene Immunization and by CpG Motif Immunostimulatory Oligodeoxynucleotides", *Allergy*, 1997:53:93–97.

* cited by examiner

METHOD FOR ENHANCING AN IMMUNE RESPONSE

This invention was made with Government support under Grant No. AI40682, awarded by the National Institutes of Health. The government has certain rights in this invention.

Throughout this application various publications are referenced. The disclosures of these publications in their entireties are hereby incorporated by reference into this application in order to describe more fully the state of the art to which this invention pertains.

TECHNICAL FIELD OF THE INVENTION

The invention relates to a method for enhancing an immune response by administering an immunostimulatory nucleotide sequence prior to antigen exposure. More particularly, the method is suited for enhancing antibody production, IFNγ release, CTL activity and Th1-related effects in response to antigen administration.

BACKGROUND OF THE INVENTION

Adjuvants are typically administered in conjunction with antigen in vaccination protocols. Adjuvants serve to amplify or modulate the immune response to a co-delivered antigen. Currently, few adjuvants (e.g., alum and MF59) have been approved for use in human vaccination.

Immunostimulatory DNA sequences (ISS) delivered in conjunction with an antigen activate innate immunity and bias the adaptive immune response toward Th1 differentiation. ISS have been used as an adjuvant to amplify the immune response to a co-delivered antigen. See, for example, WO 98/16247, and U.S. Pat. No. 5,736,524 and No. 5,780,448.

There remains a need for optimization of the nature and efficacy of vaccination and immunotherapeutic protocols.

SUMMARY OF THE INVENTION

The invention provides a method for enhancing an immune response to a substance, such as an antigen administered to a subject, or a pathogen to which the subject is exposed. The method can be used to modulate the magnitude, the duration, and the nature of the immune response to subsequent exposure to a substance. The method comprises administering an immunostimulatory nucleotide sequence (ISS) to the subject at least one hour prior to exposure to the substance by the subject. This "pre-priming" of the subject with ISS prior to antigen administration or pathogen exposure results in amplification of the Th1 immune response to the substance as compared to co-administration of ISS and antigen. Pre-priming with ISS also shifts the nature of the immune response from a Th2 type response to a Th1 type response.

Examples of an immune response that can be enhanced by the method of the invention include, but are not limited to, activation of innate immunity (e.g., macrophages, natural killer (NK) cells), a Th1 response, a cytotoxic T lymphocyte (CTL) response, and production of an antibody. The antibody response is preferably increased production of antibodies of the IgG2a subclass. The method can be used for immunizing a subject against an antigen, and provides more effective immunization than if the ISS were co-administered with the antigen. The method can be used prophylactically or therapeutically.

In preferred embodiments, the ISS comprises a CG, p(GC) or p(IC) DNA or RNA nucleotide sequence. Of these, a CG containing nucleotide sequence is preferred. Preferably, the ISS further comprises a pG nucleotide sequence. Examples of an ISS include, but are not limited to, sequences comprising 5'-rrcgyy-3' (SEQ ID NO: 1), such as AACGTT, AGCGTC, AGCGTT, GACGTT, GGCGTT, AACGTC, and AGCGTC (SEQ ID NOs: 5-11, respectively), 5'-rycgyy-3' (SEQ ID NO: 2) such as GTCGTT (SEQ ID NO: 24), 5'-rrcgyycg-3' (SEQ ID NO: 3), or 5'-rycgyycg-3' (SEQ ID NO: 4).

The ISS is preferably administered between about 6 hours and about 6 weeks prior to antigen administration, and more preferably between about 1 day and about 4 weeks prior to antigen administration. Most preferably, the ISS is administered between about 3 days and about 8 days prior to antigen administration. In a preferred embodiment of the method, the ISS is administered via a systemic route such as a dermal or intramuscular route, or via a mucosal route such as an intranasal, ophthalmic, intrarectal, intravaginal or intratracheal route.

Because pre-priming activates innate immunity, the method of the invention can be used to protect against subsequent infection by a pathogen, such as a viral, bacterial, parasitic or other infectious agent. Preferably, the substance is a pathogen or an antigen associated with an infectious disease, an allergen or a cancer. Examples of infectious disease include, but are not limited to, viral, bacterial, mycobacterial and parasitic disease.

DETAILED DESCRIPTION OF THE INVENTION

Figure 1:
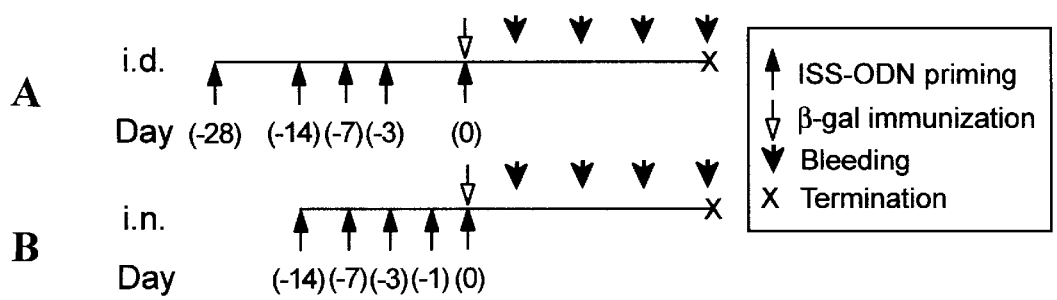
FIGS. 1a–1b is a schematic representation of the ISS pre-priming and β-gal immunization protocol described in the examples. Mice received a single i.d. or i.n. injection with ISS (50 μg) either the specified days before or with β-gal (50 μg) immunization via the same route (Day 0). Control mice received β-gal immunization without ISS. Serial bleeds occurred after β-gal immunization, and mice were sacrificed during week 7 for determination of splenocyte cytokine and CTL responses. "i.d." refers to intradermal delivery; and "i.n." to intranasal delivery.

The present invention provides an unconventional approach to amplifying the immune response in vivo. This approach provides a practical tool to amplify the immune response to subsequent antigen exposure, to activate innate immunity, to generate CTL activity and to bias the subsequent immune response toward a Th1 type of response. The invention is based on the discovery that pre-priming a subject by dissociating ISS delivery from antigen delivery significantly amplifies the immune response to antigen. This pre-priming effect is applicable to both systemic and mucosal immunization, and can be used for protection against antigens as well as against pathogens. The invention additionally provides information about the kinetics of the pre-priming effect and the optimal timing for ISS delivery for both systemic and mucosal applications.

The invention is also based on the discovery that ISS administration activates innate immunity as evidenced by increased serum levels of IFNγ and IL-12, which activate macrophages and natural killer (NK) cells, respectively. The method of the invention can thus be used for broad protection against subsequently encountered pathogens as well as against subsequently administered antigens. The combination of information about activation of innate immunity and the time course of ISS-induced enhancement of immune responses enables an effective strategy for protection against a broad range of substances.

Definitions

All scientific and technical terms used in this application have meanings commonly used in the art unless otherwise specified. As used in this application, the following words or phrases have the meanings specified.

As used herein, "immunostimulatory nucleotide sequence" or "ISS" means a polynucleotide that includes, or consists of, at least one immunostimulatory oligonucleotide (ISS-ODN) moiety. The ISS moiety is a single- or double-stranded DNA or RNA oligonucleotide having at least six nucleotide bases that may include, or consist of, a modified oligonucleotide or a sequence of modified nucleosides. The ISS moieties comprise, or may be flanked by, a CG containing nucleotide sequence or a p(IC) nucleotide sequence, which may be palindromic.

As used herein, "polynucleotide" refers to DNA or RNA and can include sense and antisense strands as appropriate to the goals of the therapy practiced according to the invention. Polynucleotide in this context includes oligonucleotides.

As used herein, "subject" refers to the recipient of the therapy to be practiced according to the invention. The subject can be any vertebrate, but will preferably be a mammal. If a mammal, the subject will preferably be a human, but may also be a domestic livestock, laboratory subject or pet animal.

As used herein, "substance" refers to any substance to which an immune response may be directed, and includes antigens and pathogens.

As used herein, "exposure" to a substance includes both natural, environmental exposure to the substance as well as administration of the substance to a subject.

As used herein, enhancing "innate immunity" includes enhancing activation of macrophages, NK cells, antigen presenting cells (APCs), and other elements known to be involved in protection against subsequent exposure to microbial pathogens. Enhancement of innate immunity can be determined using conventional assays for activation of these elements, including but not limited to assays described in the examples set forth below.

As used herein, "enhancing a Th1 immune response" in a subject is evidenced by:

(1) a reduction in levels of IL-4 or IL-5 measured before and after antigen challenge; or detection of lower (or even absent) levels of IL-4 in a treated subject as compared to an antigen-primed, or primed and challenged, control;

(2) an increase in levels of IL-12, IL-18 and/or IFN ($\alpha,\beta$ or $\gamma$) before and after antigen challenge; or detection of higher levels of IL-12, IL-18 and/or IFN ($\alpha,\beta$ or $\gamma$) in an ISS treated subject as compared to an antigen-primed or, primed and challenged, control;

(3) production of IgG2a antibody or its human analog in a treated subject;

(4) a reduction in levels of antigen-specific IgE as measured before and after antigen challenge; or detection of lower (or even absent) levels of antigen-specific IgE in an ISS treated subject as compared to an antigen-primed, or primed and challenged, control; and/or (5) induction of a cytotoxic T lymphocyte ("CTL") response in a treated subject.

Exemplary methods for determining such values are described further in the Examples. The ISS of the invention provide relatively safe, effective means of stimulating a robust immune response in a vertebrate subject against any antigen.

Methods

The invention provides a method for enhancing an immune response. The method can be used to modulate the magnitude, the duration and/or the quality of the immune response to a subsequently administered antigen or to subsequent exposure to a substance such as a pathogen. In one embodiment, the method enhances the production of antibodies that recognize the substance. Enhanced antibody production can be determined by detecting increased antibody levels in a subject or subjects pre-primed with ISS as compared to antibody levels in a subject or subject not receiving ISS prior to antigen administration. An example of a suitable assay for determining enhanced antibody production is described below in Example 1. Enhanced antibody production can also include increasing the production of one class of antibody relative to production of another, less desirable class of antibody. For example, production of IgG2a antibodies can be enhanced while levels of IgE antibodies are reduced.

The immune response can also be enhanced by shifting the response from a Th2 to a Th1 type response. As used herein, "Th1/Th2 response(s)" refer to types 1 and 2, respectively, helper T lymphocyte (Th) mediated immune responses. Th2 responses include the allergy-associated IgE antibody class as well as elevated levels of IL-4 and IL-5 cytokines by Th2 lymphocytes. Soluble protein antigens tend to stimulate relatively strong Th2 responses. Th1 cells secrete IL-2, interferon-gamma (IFN$\gamma$) and tumor necrosis factor-beta (TNF$\beta$) (the latter two of which are involved in macrophage activation and delayed-type hypersensitivity in response to antigen stimulation or infection with a pathogen).

Accordingly, Th2 associated responses can be suppressed, thereby reducing the risk of prolonged allergic inflammation and antigen-induced anaphylaxis. The enhancement of Th1 associated responses is of particular value in responding to intracellular infections because cellular immunity is enhanced by activated Th1 (IFN$\gamma$) cells. In addition, administration of polynucleotides helps stimulate production of CTL, further enhancing the immune response.

The method of the invention can be used to modulate or enhance the immune response both prophylactically and therapeutically. Thus, the invention provides a method of immunizing a subject as well as a method of immunotherapy.

The method of the invention comprises administering an ISS to a subject prior to exposure to the substance. This pre-priming is typically performed at least one hour prior to antigen administration or other exposure to a substance. The ISS is preferably administered between about 6 hours and about 6 weeks prior to antigen administration or other exposure to a substance, and more preferably between about 1 day and about 4 weeks prior to antigen administration. Most preferably, the ISS is administered between about 3 days and about 8 days prior to antigen administration. The antigen or other substance can be introduced by conventional immunization techniques, or by natural exposure.

Preferably, the substance is an antigen or a pathogen associated with an infectious disease, an allergen or a cancer. Examples of infectious disease include, but are not limited to, viral, bacterial, mycobacterial and parasitic disease. Examples of allergens include, but are not limited to, plant pollens, dust mite proteins, animal dander, saliva and fungal spores. Examples of cancer-associated antigens include, but are not limited to, live or irradiated tumor cells, tumor cell extracts and protein subunits of tumor antigens. The antigen can also be a sperm protein for use in contraception. In some embodiments, the antigen is an environmental antigen. Examples of environmental antigens include, but are not limited to, respiratory syncytial virus ("RSV"), flu viruses and cold viruses.

Structure and Preparation of ISS

The ISS of the invention includes an oligonucleotide, which can be a part of a larger nucleotide construct such as a plasmid or bacterial DNA. The term "polynucleotide-"therefore includes oligonucleotides, modified oligonucleotides and oligonucleosides, alone or as part of a larger construct. The polynucleotide can be single-stranded DNA (ssDNA), double-stranded DNA (dsDNA), single-stranded RNA (ssRNA) or double-stranded RNA (dsRNA). The ISS can include bacterial DNA, which provides ISS activity.

The polynucleotide portion can be linearly or circularly configured, or the oligonucleotide portion can contain both linear and circular segments. Modifications of oligonucleotides include, but are not limited to, modifications of the 3'OH or 5'OH group, modifications of the nucleotide base, modifications of the sugar component, and modifications of the phosphate group.

The ISS can comprise ribonucleotides (containing ribose as the only or principal sugar component), deoxyribonucleotides (containing deoxyribose as the principal sugar component), or in accordance with the established state-of-the-art, modified sugars or sugar analogs may be incorporated in the oligonucleotide of the present invention. Examples of a sugar moiety that can be used include, in addition to ribose and deoxyribose, pentose, deoxypentose, hexose, deoxyhexose, glucose, arabinose, xylose, lyxose, and a sugar "analog" cyclopentyl group. The sugar may be in pyranosyl or in a furanosyl form. In the modified oligonucleotides of the present invention, the sugar moiety is preferably the furanoside of ribose, deoxyribose, arabinose or 2'-O-methylribose, and the sugar may be attached to the respective heterocyclic bases either in I or J anomeric configuration.

The phosphorous derivative (or modified phosphate group) that can be attached to the sugar or sugar analog moiety in the modified oligonucleotides of the present invention can be a monophosphate, diphosphate, triphosphate, alkylphosphate, alkanephosphate, phosphoronthioate, phosphorodithioate or the like. The heterocyclic bases, or nucleic acid bases that are incorporated in the oligonucleotide base of the ISS can be the naturally occurring principal purine and pyrimidine bases, (namely uracil or thymine, cytosine, adenine and guanine, as mentioned above), as well as naturally occurring and synthetic modifications of said principal bases. Those skilled in the art will recognize that a large number of "synthetic" non-natural nucleosides comprising various heterocyclic bases and various sugar moieties (and sugar analogs) are available, and that the ISS can include one or several heterocyclic bases other than the principal five base components of naturally occurring nucleic acids. Preferably, however, the heterocyclic base in the ISS is selected from uracil-5-yl, cytosin-5-yl, adenin-7-yl, adenin-8-yl, guanin-7-yl, guanin-8-yl, 4-aminopyrrolo [2,3-d] pyrimidin-5-yl, 2-amino-4-oxopyrolo [2,3-d] pyrimidin-5-yl, 2-amino-4-oxopyrolo [2,3-d] pyrimidin-3-yl groups, where the purines are attached to the sugar moiety of the oligonucleotides via the 9-position, the pyrimidines via the 1-position, the pyrrolopyrimidines via the 7-position and the pyrazolopyrimidines via the 1-position.

Structurally, the root oligonucleotide of the ISS is a non-coding sequence that can include at least one unmethylated CpG motif. The relative position of any CpG sequence in ISS with immunostimulatory activity in certain mammalian species (e.g., rodents) is 5'-CG-3' (i.e., the C is in the 5' position with respect to the G in the 3' position).

Some oligonucleotide ISS (ISS-ODN) are known. In such ISS-ODN, the CpG motif is flanked by at least two purine nucleotides (e.g., GA or AA) and at least two pyrimidine nucleotides (5'-r-r-[C]-[G]-y-y-3'; SEQ ID NO: 1), or flanked by a purine and a pyrimidine 5' to the CG (5'-r-y-[C]-[G]y-y-3'; SEQ ID NO: 2), wherein the pyrimidine 5' to the CG is preferably T. CpG motif-containing ISS-ODN are believed to stimulate B lymphocyte proliferation (see, e.g., Krieg, et al., Nature, 374:546–549, 1995).

The core hexamer structure of the foregoing ISS can be flanked upstream and/or downstream by any number or composition of nucleotides or nucleosides. However, ISS are at least 6 bases in length, and preferably are between 6 and 200 bases in length, to enhance uptake of the ISS into target tissues. Those of ordinary skill in the art will be familiar with, or can readily identify, reported nucleotide sequences of known ISS-ODN for reference in preparing ISS. For ease of reference in this regard, the following sources are especially helpful: Yamamoto, et al., Microbiol. Immunol., 36:983 (1992); Ballas, et al., J.Immunol., 157:1840 (1996); Klinman, et al., J.Immunol., 158:3635 (1997); Sato, et al., Science, 273:352 (1996).

In particular, ISS useful in the invention include those that have hexameric nucleotide sequences having "CpG" motifs. Although DNA sequences are preferred, RNA ISS can be used, with inosine and/or uracil substitutions for nucleotides in the hexamer sequences.

For example, DNA based ISS useful in the invention include those that have the following hexameric nucleotide sequences:

AACGTT, AGCGTC, AGCGTT, GACGTT, GGCGTT, AACGTC, AGCGTC, GACGTC, GGCGTC, AACGCC, AGCGCC, GACGCC, GGCGCC, AGCGCT, GACGCT, GGCGCT, TTCGAA, GGCGTT, AACGCC, and GTCGTT (SEQ ID NOs: 5–24, respectively).

Also useful are octamers in the form of 5'-rrcgyycg-3' (SEQ ID NO: 3), such as AGCGTCCG, AACGTTCG, AGCGTTCG, GACGTTCG, GGCGTTCG, AACGTTCG, and AGCGTCCG (SEQ ID NOs : 25–31, respectively), and in the form of 5'-rycgyycg-3' (SEQ ID NO: 4), wherein the y is preferably "t", larger ISS-ODN having a second CG further 3' to the core hexameric sequence, and bacterial DNA, which are enriched with ISS.

The ISS may or may not include palindromic regions. If present, a palindrome may extend only to a CpG motif, if present, in the core hexamer sequence, or may encompass more of the hexamer sequence as well as flanking nucleotide sequences.

In addition, backbone phosphate group modifications (e.g., methylphosphonate, phosphorothioate, phosphoroamidate and phosphorodithioate internucleotide linkages) can confer anti-microbial activity on the ISS and enhance their stability in vivo, making them particularly useful in therapeutic applications. A particularly useful phosphate group modification is the conversion to the phosphorothioate or phosphorodithioate forms of ISS. In addition to their potentially anti-microbial properties, phosphorothioates and phosphorodithioates are more resistant to degradation in vivo than their unmodified oligonucleotide counterparts, making the ISS of the invention more available to the subject.

ISS can be synthesized using techniques and nucleic acid synthesis equipment that are well-known in the art. For reference in this regard, see, e.g., Ausubel, et al., Current Protocols in Molecular Biology, Chs. 2 and 4 (Wiley Interscience, 1989); Maniatis, et al., Molecular Cloning: A Laboratory Manual (Cold Spring Harbor Lab. New York, 1982); U.S. Pat. No. 4,458,066 and U.S. Pat. No. 4,650,675. Because the ISS is non-coding, there is no concern about maintaining an open reading frame during synthesis.

Alternatively, ISS can be isolated from microbial species (especially mycobacteria) using techniques well-known in the art, such as nucleic acid hybridization. Whole or fragmented bacterial DNA can be used. Preferably, such isolated ISS will be purified to a substantially pure state; i.e., to be free of endogenous contaminants, such as lipopolysaccharides.

Compositions

The invention provides compositions that are useful for treating and preventing disease, such as allergy, cancer or infection. In one embodiment, the composition is a pharmaceutical composition. The composition is preferably an immunotherapeutic composition. The composition can comprise a therapeutically or prophylactically effective amount of an ISS of the invention, as described above. The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention.

Administration and Dosage

In a preferred embodiment of the method, the ISS is administered via a systemic or mucosal route, or directly into a specific tissue, such as the liver, bone marrow, or into the tumor in the case of cancer therapy. Examples of systemic routes include, but are not limited to, intradermal, intramuscular, subcutaneous and intravenous administration. Examples of mucosal routes include, but are not limited to, intranasal, intravaginal, intrarectal, intratracheal and ophthalmic administration. Mucosal routes, particularly intranasal, intratracheal and ophthalmic, are preferred for protection against natural exposure to environmental pathogens such as RSV, flu viruses and cold viruses or to allergens such as grass and ragweed pollens and house dust mites. The local activation of innate immunity by ISS will enhance the protective effect against a subsequently encountered substance, such as an antigen, allergen or microbial agent.

Treatment includes prophylaxis and therapy. Prophylaxis or therapy can be accomplished by a single direct administration at a single time point or multiple time points. Administration can also be delivered to a single or to multiple sites.

The subject can be any vertebrate, but will preferably be a mammal. Mammals include human, bovine, equine, canine, feline, porcine, and ovine animals. If a mammal, the subject will preferably be a human, but may also be a domestic livestock, laboratory subject or pet animal.

The dose of ISS administered to a subject, in the context of the present invention, should be sufficient to effect a beneficial therapeutic response in the subject over time, or to inhibit growth of cancer cells, to inhibit allergic responses or to inhibit infection. Thus, ISS is administered to a patient in an amount sufficient to elicit an effective immune response to the specific antigens and/or to alleviate, reduce, cure or at least partially arrest symptoms and/or complications from the disease or infection.

An amount adequate to accomplish this is defined as a "therapeutically effective dose."

A particular advantage of the ISS of the invention is their capacity to exert immunomodulatory activity even at relatively minute dosages. Although the dosage used will vary depending on the clinical goals to be achieved, a suitable dosage range is one that provides up to about 1–1000 μg of ISS/ml of carrier in a single dosage. Alternatively, a target dosage of ISS can be considered to be about 1–10 μM in a sample of subject blood drawn within the first 24–48 hours after administration of ISS. Based on current studies, ISS are believed to have little or no toxicity at these dosage levels.

In this respect, it should be noted that the anti-inflammatory (anti-allergenic), anti-microbial and immunotherapeutic activities of ISS in the invention are essentially dose-dependent. Therefore, to increase ISS potency by a magnitude of two, each single dose is doubled in concentration. Clinically, it may be advisable to administer the ISS in a low dosage (e.g., about 1 μg/ml to about 50 μg/ml), then increase the dosage as needed to achieve the desired therapeutic goal. Some routes of administration, such as via ophthalmic drops, will require higher concentrations. Those skilled in the art can adjust the dosage and concentration to suit the particular route of delivery.

In view of the teaching provided by this disclosure, those of ordinary skill in the clinical arts will be familiar with, or can readily ascertain, suitable parameters for administration of ISS according to the invention.

EXAMPLES

The following examples are presented to illustrate the present invention and to assist one of ordinary skill in making and using the same. The examples are not intended in any way to otherwise limit the scope of the invention.

Example 1

ISS Pre-Priming Elicits Extended Th1-Biased Immune Responses

This example demonstrates that ISS provide Th1 adjuvant activity for an extended period of time after delivery. ISS were administered intradermally (i.d.) up to 28 days prior to a primary i.d. immunization with β-galactosidase (β-gal), and enhanced antibody production, antigen-specific cytokine production and CTL response were measured.

Methods

Immunization Reagents

β-gal, lipopolysaccharide (LPS), and cholera toxin (CT) (Sigma, St Louis, Mo.), ISS-ODN and mutated phosphorothioate oligodeoxynucleotide (M-ODN) (Trilink Biotechnologies, San Diego. Calif.) were used to immunize mice. The ISS-ODN used in these studies has the following sequence:
5'-TGACTGTGAACGTTCGAGATGA-3' (SEQ ID NO: 32). The M-ODN has the sequence 5'-TGACTGTG AACCTTAGAGATGA-3' (SEQ ID NO: 33).

Immunization Protocols

Female BALB/c mice, aged 6–8 weeks, were purchased from Jackson Laboratory (Bar Harbor, Me.) and were used in all experiments. The i.d. and i.n. immunization protocols used in these experiments are outlined in FIG. 1. In brief, ISS-ODN was delivered to mice from 28 days to 1 day prior to or with β-gal. Mice received a single i.d. injection with ISS (50 μg) either the specified day before or with i.d. β-gal (50 μg) immunization. Control mice received i.d. β-gal immunization alone or with M-ODN. Splenocytes were harvested from sacrificed mice during week 7. Intradermal injections were performed at the base of the tail in 50 μl of saline. Mice were anaesthetized for i.n. delivery of reagents with Metophane (Mallinckrodt Veterinary Inc., Mundelein, Ill.) and 15 μl of saline with reagents was delivered to each nare. In some experiments 50 μg of ISS-ODN, M-ODN, or LPS were injected i.d., and serum and, spleens were collected at times ranging from 1–14 days after injection to assess in vivo immune activation.

Collection of Samples

Blood was obtained by retro-orbital bleed, serum was spun and then stored at −70° C. until IgG2a, IgG1, or IFNγ assay.

Antibody Assays

Serum was used in ELISA assays for antigen specific immunoglobulin as described previously. Results are expressed in units/ml (U/ml) based on pooled high titer anti-β-gal standards obtained from mice receiving multiple immunizations. The undiluted serum IgG standards were given an arbitrary concentration of 400,000 U/ml. Ninety-six-well plates were coated with 5 μg of β-gal (Sigma) in 50 μl borate buffered saline (BBS; pH 9.2) overnight at 4° C. Plates were then incubated with 1% BSA in BBS for 2 hours at 37° C. Plates were washed twice with BBS/0.5% Tween 20 (Sigma) and incubated with samples overnight at 4° C. Plates were washed 8 times with BBS/Tween 20 and incubated with alkaline phosphatase-linked anti-IgG1 or IgG2a (Southern Biotechnologies, Birmingham, Ala.) for 2 hours at room temperature. The plates were then washed 8 times with BBS/Tween 20 and incubated with a solution of p-nitrophenyl phosphate (1 mg/ml; Boehringer Mannheim). Absorbance at 405 nm was read at 1 hour and compared to the standard curve on each plate using the DeltaSOFT II v. 3.66 program (Biometallics, Princeton, N.J.).

Cytokine Assays

Mouse spleens were harvested at week 8 for CTL and cytokine assays. Three days before setting up cytokine assays mice were i.v. boosted with 10 μg β-gal. Mice were sacrificed by cervical dislocation. Spleens were harvested and teased to make single cell preparations. Splenocyte cytokine profiles were analyzed by incubation of $5 \times 10^5$ splenocytes in 96-well plates in a final volume of 200 μl of supplemented RPMI 1640 with β-gal added at 10 μg/ml, at 37° C./5% $CO_2$ as previously described. Culture supernatants were harvested at 72 hours and analyzed by ELISA. Pharmagen (San Diego, Calif.) anti-IFNγ and anti-IL12 capture and detection antibodies, recombinant IFNγ and IL-12, were all used per the manufacturer's recommendations. A standard curve was generated on each plate using known amounts of recombinant IFNγ and each culture supernatant was compared to the standard curve on the plate using the DeltaSOFT II v. 3.66 program.

CTL Assays

Seven million splenocytes from immunized mice were incubated with $6 \times 10^6$ mitomycin-C treated naive splenocytes in the presence of recombinant human IL-2 and class I $H2^d$ restricted β-gal nanopeptide (T-P-H-P-A-R-I-G-L; SEQ ID NO: 34). in supplemented RPMI 1640 with 10% FCS at 37° C./5% $CO_2$, as previously described. After 5 days, re-stimulated cells were harvested and debris was removed by centrifugation on a lympholyte M (Accurate Chemicals, Westbury, N.Y.) gradient. Specific lysis was measured by aliquotting effector cells with $H2^d$ restricted p815 peptide pulsed target cells at 25:1, 5:1, and 1:1 ratios. Controls for specific lysis included non-pulsed p815 cells, and p815 cells pulsed with an irrelevant influenza nucleoprotein peptide. Cells were incubated for 4 hours in clear 2% BSA supplemented RPMI 1640 in round bottom plates. Total and specific lysis were measured using the Promega Cytotox 96 kit (Madison, Wis.). The assay system measures lactate dehydrogenase (LDH) release using a substrate metabolized by LDH into a colored by-product. The equation used to calculate specific lysis was (target lysis−non-specific lysis)/(total lysis)×100.

Statistics

Statistical analysis of results was conducted using Statview computer software (Abacus Concepts, Grand Rapids, Mich.). A two-tailed Student's t test was used to establish p values, and those having p values $\leq 0.05$ were considered significant.

Results

Figure 2A:
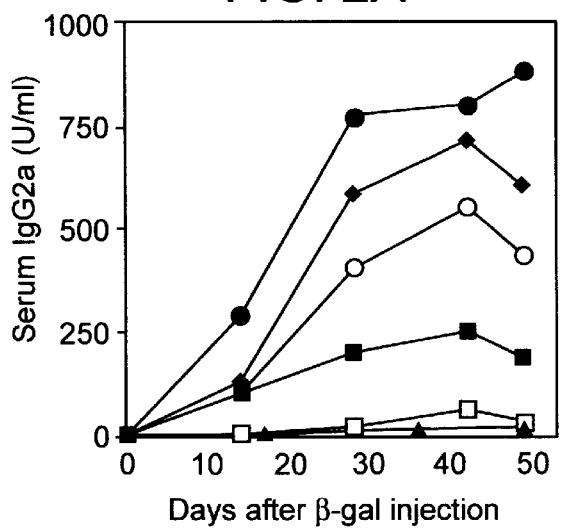
FIG. 2A is graph showing time course of IgG2a production after i.d. ISS pre-priming and β-gal immunization. Mice received either no ISS (open squares), ISS on day 0 (open circles), day −3 (closed diamonds), day −7 (closed circles), day −14 (closed squares), or day −28 (closed triangles) relative to β-gal. Mice were bled at serial time points to establish the kinetics of IgG2a production. Results represent mean values for 4 mice per group and error bars reflect standard errors of the means. Results are representative of 3 similar and independent experiments.
Figure 2B:
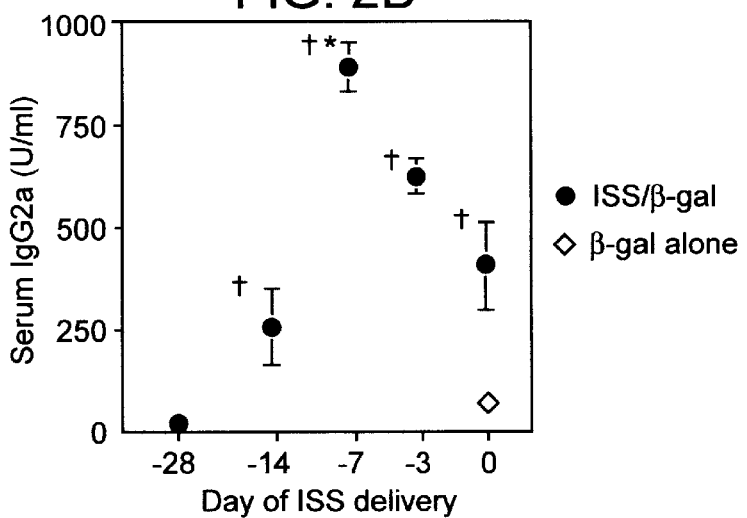
FIG. 2B is graph showing serum IgG2a after i.d. ISS pre-priming and β-gal immunization at 7 weeks post immunization. The open diamond represents data for mice receiving β-gal alone, and the closed circles represent data for mice receiving ISS at the indicated day relative to β-gal administration. Results represent mean values for 4 mice per group and error bars reflect standard errors of the means. Results are representative of 3 similar and independent experiments. Mice receiving ISS up to 14 days prior to β-gal demonstrated an improved IgG2a response when compared to mice immunized with β-gal alone (†; p≦0.05). Mice receiving ISS 7 days before β-gal immunization had a significantly improved IgG2a response when compared to mice co-administered ISS with β-gal (★; p≦0.05).
Figure 2C:
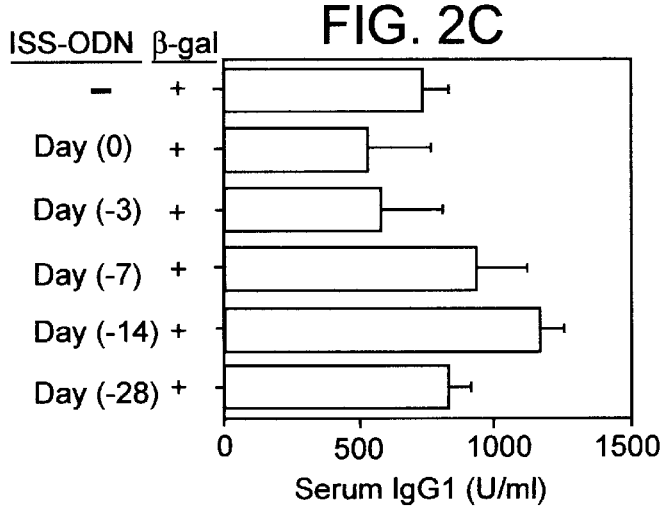
FIG. 2C is graph showing serum IgG1 after i.d. ISS pre-priming and β-gal immunization at 7 weeks post immunization. Results represent mean values for 4 mice per group and error bars reflect standard errors of the means. Results are representative of 3 similar and independent experiments.

Analysis of the IgG2a response of immunized mice demonstrated that ISS provides a prolonged window of adjuvant activity (FIG. 2A). When compared to immunization with β-gal alone, mice receiving ISS up to 14 days prior to β-gal had a significant increase in their serum IgG2a response. Furthermore, the IgG2a response was improved over ISS/β-gal co-immunization if ISS-ODN was given 3–7 days before antigen, and statistical significance was reached if ISS-ODN delivered 7 days before antigen (p<0.05 for week 6 IgG2a levels) (FIG. 2B). Of note, the relatively IL-4 dependent IgG1 response was not increased by ISS pre-priming or by co-delivery with β-gal (FIG. 2C). Mice immunized with M-ODN either prior to or with β-gal immunization did not demonstrate an improved IgG2a or IgG1 response when compared to mice immunized with β-gal alone.

Figure 3A:
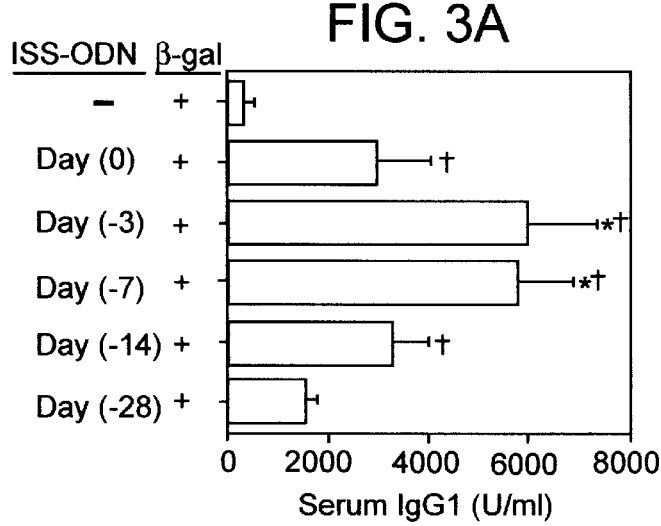
FIG. 3A is a bar graph showing the splenocyte IFNγ response after i.d. ISS pre-priming and β-gal immunization. Results represent the mean for 4 mice in each group and similar results were obtained in 2 other independent experiments. Error bars reflect standard errors of the means. Mice receiving ISS up to 14 days prior to β-gal demonstrated an improved IFNγ response when compared to mice immunized with β-gal alone (†; $p \leq 0.05$). Delivery of ISS from 3–7 days before β-gal led to an improved IFNγ response when compared to mice receiving ISS/β-gal co-immunization (★; $p \leq 0.05$).
Figure 3B:
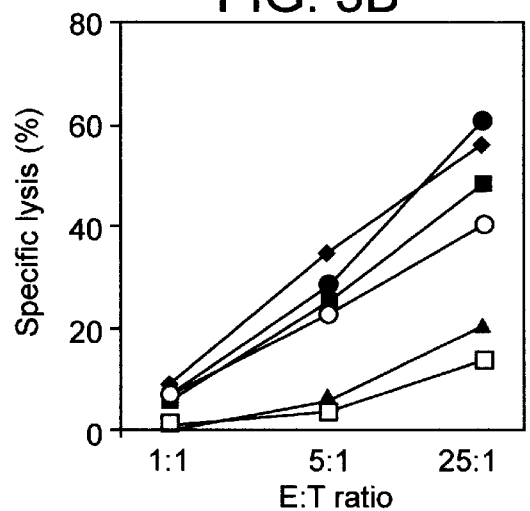
FIG. 3B is a graph showing the splenocyte CTL response after i.d. ISS pre-priming and β-gal immunization. Mice received either no ISS (open squares), ISS on day 0 (open circles), day −3 (closed diamonds), day −7 (closed circles), day −14 (closed squares), or day −28 (closed triangles) relative to β-gal. Results represent the mean for 4 mice in each group and similar results were obtained in 2 other independent experiments. Error bars reflect standard errors of the means.
Figure 3C:
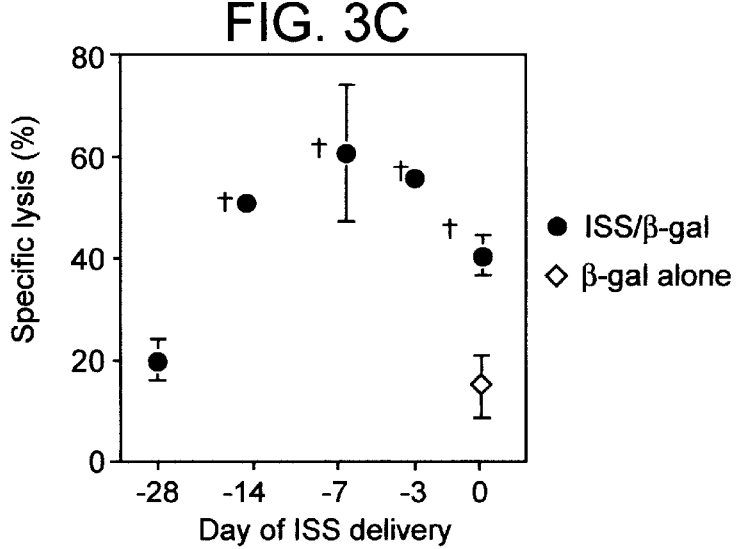
FIG. 3C is a plot showing a comparison of CTL response at an effector:target ratio of 25:1. The open diamond represents data for mice receiving β-gal alone, and the closed circles represent data for mice receiving ISS at the indicated day relative to β-gal administration. Mice receiving ISS up to 14 days prior to β-gal demonstrated an improved CTL response when compared to mice immunized with β-gal alone (†; $p \leq 0.05$).

The effect of ISS pre-priming on cellular immune responses was next evaluated. Splenocytes were harvested from immunized mice during week 8, and utilized in both cytokine and CTL assays FIGS. 3A-3C). Antigen specific IL-4 production was significantly increased in mice pre-primed up to 14 days before β-gal immunization compared to mice immunized with antigen alone (p<0.05). In addition, mice ISS pre-primed 3–7 days before β-gal immunization demonstrated a 100% increase in their IFNγ response compared to mice co-immunized with ISS and β-gal (p<0.05).

Further studies evaluated the CTL response of mice after ISS pre-priming. The results again demonstrate a prolonged window of ISS adjuvant activity. Delivery of ISS up to 14 days before β-gal vaccination led to a significantly improved CTL response over β-gal vaccination without adjuvant (p<0.05). ISS pre-priming at day −7 and day −3 resulted in a trend toward improved response, but did not lead to a statistically significant increase in CTL activity when compared to ISS/β-gal co-immunization. Mice immunized with M-ODN either prior to or with β-gal immunization did not demonstrate an improved IFNγ or CTL response when compared to mice immunized with β-gal alone.

The data presented in this example demonstrate that i.d. delivery of ISS, up to 2 weeks prior to i.d. β-gal administration, results in an improved Th1 biased immune response relative to i.d. vaccination with antigen alone. Anti-β-gal IgG2a (Th1 isotype), IFNγ release by antigen specific T cells, and CTL activity against peptide pulsed target cells, are all higher in mice pre-primed (up to 14 days) with ISS compared to mice immunized with β-gal alone. The pre-priming effect was diminished when the interval between ISS and antigen delivery was extended to 28 days. Interestingly, the optimal immune response is seen in mice pre-primed with ISS 3–7 days prior to β-gal injection and not in mice co-delivered ISS and β-gal. A 3–7 day ISS pre-priming interval results in anti-β-gal IgG2a levels and β-gal specific IFNγ responses which are approximately twice as high as those seen in ISS/β-gal co-immunized mice.

Example 2

ISS Activate the Immune System For Up to 14 Days

This example demonstrates that serum levels of the type 1 cytokines IL-12 and IFNγ are elevated for extended periods following injection of ISS into naive mice. The data presented here show that the duration and peak expression of these intercellular signaling molecules correlate well with the duration and peak of the ISS pre-priming effect.

Methods

Serum levels of IL-12 and IFNγ were measured in naive mice before and 1–14 days after i.d. injection of ISS alone. The materials and assays used were the same as those described above in Example 1. In addition, the time course of peak in vivo splenocyte cytokine production after ISS delivery was evaluated using RT-PCR to measure IL-12 p40 and IFNγ mRNA expression. Flow cytometry was used to measure the level of expression of various co-activation molecules on B cells from mice injected with ISS. The molecules examined include class I and II, CD40 and B7.2. To control for auto-fluorescence and non-specific antibody staining, isotype control antibodies were used.

Mice were i.d. injected with 50 μg of ISS on day 0. Control mice received LPS (50 μg) or nothing. At serial time points after injection, serum was obtained and cytokine levels were analyzed by ELISA.

RT-PCR

For cytokine mRNA analysis, total cellular RNA was extracted from splenocytes using the Stratagene RNA Isolation Kit, (San Diego, Calif.) and subjected to semi-quantitative RT-PCR. First-strand cDNA preparation and PCR amplification were performed using the SuperScript Preamplification system (GibcoBRL, Gaithersburg, Md.) and Advan Taq Plus DNA Polymerase (Clontech, San Fransisco, Calif.), respectively. The primer sequences used were: IL-12p4O sense 5'-GGGACATCATCAAACCAGACC-3' (SEQ ID NO: 35), and antisense 5'-GCCAACCAAGCAGAAGACAGC-3' (SEQ ID NO: 36); IFNγ sense 5'-TGCATCTTGGCTTTGCAGCTCTTCCTCATGGC-3' (SEQ ID NO: 37), and antisense 5'TGGACCTGTGGGTTGTTGACCTCAAACTTGGC-3' (SEQ ID NO: 38); and GAPDH sense 5'-ACCACAGTCCATGCCATCAC-3' (SEQ ID NO: 39) and antisense, 5'-TCCACCACCCTGTTGCTGTA-3' (SEQ ID NO: 40).

PCR products were visualized by electrophoresis on 2% agarose gels after staining with ethidium bromide.

Flow Cytometry

At serial time points after injection, mice were sacrificed and spleens were harvested and made into single cell suspensions. Cells were stained with B220 to identify B cells and with FI TC labeled antibodies to detect co-stimulatory molecules identified in the Table 2. Live cells (propidium iodide-negative) were analyzed by flow cytometry (Becton Dickinson, San Jose, Calif.).

The flow cytometry methods used in this example have been described by Martin-Orozco E et al., 1999, Enhancement of Antigen Presenting Cell Surface Molecules Involved in Cognate Interactions by Immunostimulatory DNA Sequences (ISS), *Int. Immunol.* 11 (in press). Briefly, following incubation with Fc block (PharMingen, San Diego, Calif.), sample cells were stained with PE conjugated antibodies specific for B cells (anti-B220, PharMingen) and with FITC conjugated antibodies specific for the following surface molecules: anti-MHC class 1, class II, CD16/32, CD40, CD80, and CD86 (PharMingen). Isotype controls for the specific surface markers are as follows, Hamster IgG, Hamster IgM, Rat IgG2a, Rat IgG2b, Rat IgM, Mouse IgG2&, Mouse IgG2b (Cal Tag or PharMingen). Propidium iodide was included in the last wash at a concentration of 2 μg/ml. Live cells (propidium iodide-negative) were analyzed on a FACSCalibur flow cytometer (Becton Dickinson, San lose, Calif.). The data were analyzed with Cell Quest (Becton Dickinson) and FlowJo (Tree Star, San Carlos, Calif.) software.

Immunostimulatory oligodeoxynucleotide treatment significantly increased non-specific antibody binding or autofluorescence (seen as increases in isotype control antibody-stained mean fluorescence), so this was controlled for with the mean fluorescence intensity ratio (MFIR; mean fluorescence when stained for surface molecule/mean fluorescence when stained with isotype control antibody). The MFIR represents the fold increase in surface marker expression relative to background autofluorescence and nonspecific antibody binding. MFIR provides a conservative and accurate estimate of expression of surface molecules when studying cells treated with ISS-containing DNA.

Results

Serum levels of cytokines measured in naive mice before and 1–14 days after i.d. injection of ISS alone are shown in Table 1. The data presented in Table 1 represent means for 2 mice per group plus or minus the standard error of the mean. The results show that i.d. injection of ISS into mice leads to elevated serum IL-12 and IFNγ levels for up to 2 weeks after delivery. These results are consistent with the 14 day window of ISS adjuvant noted with the antigen specific immune response. However, peak serum levels of IL-12 and IFNγ were seen 1 day after ISS delivery and serum IgG2a levels and splenocyte cytokine and CTL responses were highest in mice pre-primed with ISS 3–7 days before β-gal immunization.

TABLE 1

In vivo cytokine production induced by ISS-ODN

| ISS-ODN | IL-12 (pg/ml) | IFNγ (pg/ml) |
| --- | --- | --- |
| None | <42 | <14 |
| Day (1) | 4028 ± 1878 | 343 ± 83 |
| Day (3) | 2356 ± 464 | 312 ± 101 |
| Day (7) | 2034 ± 288 | 174 ± 36 |
| Day (14) | 763 ± 255 | 35 ± 71 |
| LPS Day 7 | <42 | <14 |

Figure 4:
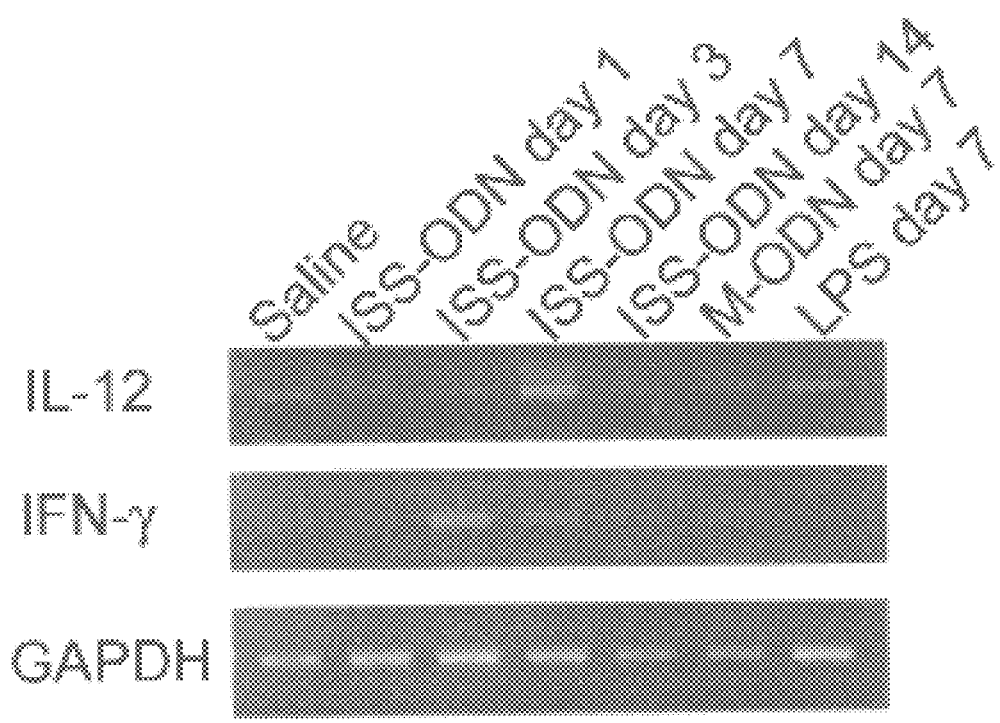
FIG. 4 shows splenocyte cytokine mRNA expression. Mice were i.d. injected with 50 μg of ISS on day 0. Control mice received either LPS (50 μg) or nothing. At serial time points after injection, mice were sacrificed, splenocytes were isolated, and subjected to RT-PCR. PCR products were visualized by electrophoresis on 2% agarose gels and staining with ethidium bromide.

Because many of the antigen specific immune responses which characterize the ISS pre-priming effect were measured in spleen, the time course of peak in vivo splenocyte cytokine production after ISS delivery was examined. Using RT-PCR, the time course for peak splenocyte IL12 p40 and IFNγ mRNA expression was assessed. Intradermal ISS delivery led to peak levels of IL12 p40 and IFNγ mRNA at 7 and 3 days, respectively (FIG. 4). These time points fall within the window identified for the maximal ISS pre-priming effect on antigen specific immunity.

Previous reports have shown that a number of co-activation molecules on B cells and APCs are up-regulated by ISS. The relatively long ISS pre-priming effect could be mediated by up-regulation of these surface proteins. Experiments were designed to establish if i.d. ISS injection would lead to a detectable and prolonged increase in the expression of these molecules in vivo. Flow cytometry was used to measure the level of expression of various co-activation molecules on 13 cells from ISS injected mice. To control for auto-fluorescence and non-specific antibody staining, isotype control antibodies were used and the results are presented as mean fluorescence intensity ratio (MFIR; MFI of antibody of interest/MFI of isotype control).

As shown in Table 2, ISS increased the expression of a number of co-activation molecules such as class I and II, CD40, and B7.2 on the surface of B cells from ISS injected mice. The time course for up-regulation of these surface proteins was extended and peak co-stimulatory molecule expression was seen 3–7 days after ISS injection. These results were consistent with the splenocyte cytokine RT-PCR results, and the 3–7 day interval between ISS pre-priming and β-gal vaccination which led to maximal antigen specific immunity.

TABLE 2

Up-regulation of cell surface molecules in vivo by ISS-ODN

| ISS | H-2K$^d$ (MHC class I) | I-A$^d$ (MHC class II) | CD16/ CD32 | CD40 | CD54 (ICAM-1) | CD80 (B7-1) | CD86 (B7.2) |
| --- | --- | --- | --- | --- | --- | --- | --- |
| None | 25.3 | 77.9 | 7.26 | 11.4 | 4.5 | 2.85 | 1.75 |
| Day 3 | 27.1 | 87.1 | 9.3 | 11.7 | 7.68 | 2.85 | 2.18 |
| Day 7 | 27.7 | 118 | 8.23 | 12.4 | 7.98 | 2.64 | 2.12 |
| Day 14 | 30.1 | 94.9 | 7.26 | 9.5 | 6.36 | 2.37 | 1.97 |

Example 3

Mucosal ISS Pre-Priming Enhances Th1 and IgA Adjuvant Activity

This example shows that other forms of immunity, e.g. mucosal immunity, can be enhanced by pre-priming with ISS. The example also shows that intranasal (i.n.) delivery of ISS can modulate both systemic and mucosal immune responses.

Methods

The materials and assays used were as described above in Example 1. Mice received a single i.n. injection with ISS (50 μg) either the specified day before or with i.n. β-gal (50 μg) immunization. Control mice received i.n. β-gal immunization alone or in conjunction with M-ODN. Splenocytes were harvested from sacrificed mice during week 7.

Bronchoalveolar lavage fluid (BALF) was used in ELISA assays for antigen specific immunoglobulin. Fecal IgA standards were given arbitrary concentrations of 20,000 U/ml. BALF was obtained by cannulation of the trachea of sacrificed mice during week 8. The lungs were then flushed with 0.8ml of PBS. The return was spun to remove cellular debris, and frozen at −70° C. until IgA assay.

Results

Figure 5A:
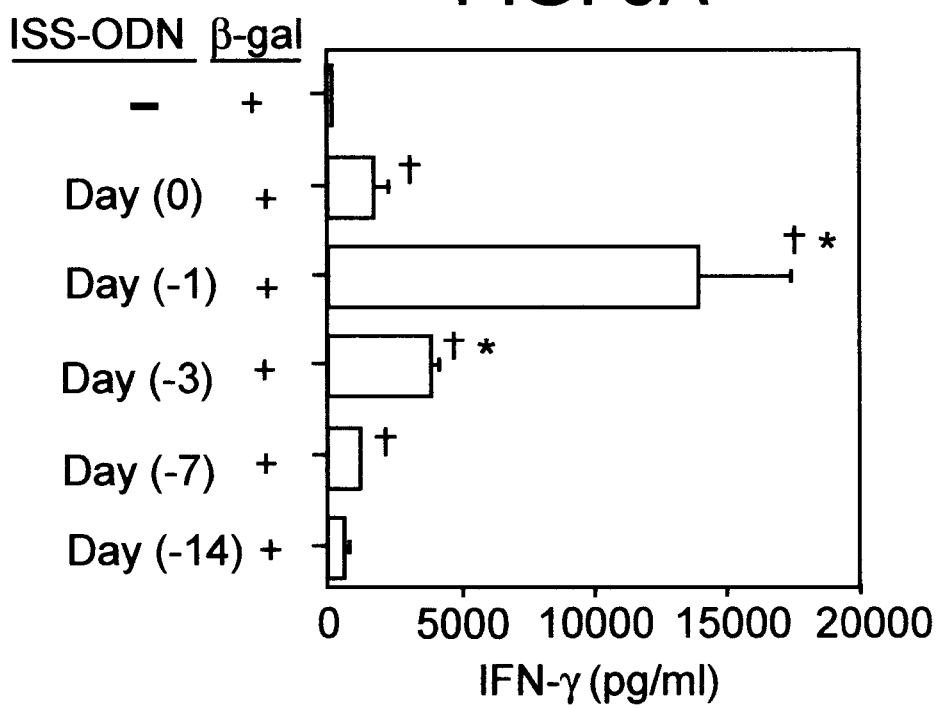
FIG. 5A is a bar graph showing splenocyte IFNγ response after i.n. ISS pre-priming and β-gal immunization. Results represent the mean for 4 mice in each group and similar results were obtained in 2 other independent experiments. Error bars reflect standard errors of the means. Mice receiving ISS up to 7 days prior to β-gal demonstrated an improved IFNγ response when compared to mice immunized with β-gal alone (†; $p \leq 0.05$). Delivery of ISS from 1–3 days before β-gal led to an improved IFNγ response when compared to mice receiving ISS/β-gal co-immunization (★; $p \leq 0.05$).
Figure 5B:
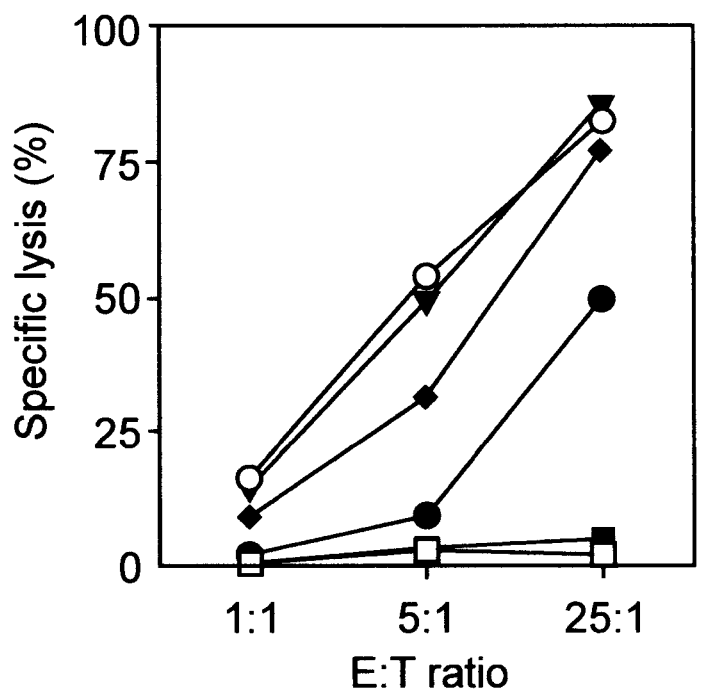
FIG. 5B is a graph showing splenocyte CTL response after i.n. ISS pre-priming and β-gal immunization. Mice received either no ISS (open squares), ISS on day 0 (open circles), or day −1 (closed triangles), day −3 (closed diamonds), day −7 (closed circles), or day −14 (closed squares) relative to β-gal. Results represent the mean for 4 mice in each group and similar results were obtained in 2 other independent experiments. Error bars reflect standard errors of the means. Mice receiving ISS up to 7 days prior to β-gal demonstrated statistically improved CTL responses at effector:target ratios of 5:1 and 25:1 when compared to mice immunized with β-gal alone ($p \leq 0.05$).

Table 3 and FIG. 5 show that i.n. pre-priming provides a 7 day window of systemic Th1 and mucosal IgA adjuvant activity. This window of adjuvant activity is shorter than when reagents are delivered i.d. Nonetheless, all immune parameters were significantly higher if mice received ISS within the week preceding or with β-gal than if mice were immunized with β-gal alone. Mice immunized with M-ODN either prior to or with β-gal immunization did not demonstrate an improved IFNγ or CTL response when compared to mice immunized with β-gal alone. The pre-priming effect observed on the BALF IgA response was modest but prolonged (1 week). Recognizing that without adjuvant the immune response to simple protein antigens such as β-gal is negligible, the week long ISS pre-priming effect with i.n. delivery is significant.

TABLE 3

Anti-β-gal Ig production induced by mucosal pre-priming and immunization

| ISS-ODN | β-gal | Serum IgG2a (U/ml) | BALF IgA (U/ml) |
|---|---|---|---|
| — | + | <500 | <50 |
| Day (0) | + | 239000 ± 71500 | 2940 ± 825 |
| Day (−1) | + | 322000 ± 112000 | 463 ± 47 |
| Day (−3) | + | 38000 ± 3490 | 398 ± 38 |
| Day (−7) | + | 17800 ± 4830 | 459 ± 183 |
| Day (−14) | + | <500 | <50 |

A stronger i.n. ISS pre-priming effect was observed on the anti-β-gal IgG2a levels, CTL activity and antigen specific IFNγ responses. Immunostimulatory oligodeoxynucleotide pre-priming at day −1 improved the IgG2a response slightly and the antigen specific splenocyte IFNγ response was improved significantly (p<0.05) compared to i.n. co-immunization with ISS and β-gal. These results demonstrate that ISS pre-priming is also effective with mucosal delivery, although the duration and the optimal interval between ISS and β-gal delivery were different than with i.d. delivery.

Discussion

A previous epidemiological study conducted on approximately 1000 Japanese school children documented a correlation between exposure to Mycobacteria tuberculosis (MTH) and a Th1 biased serum cytokine profile in study subjects. In addition, purified protein derivative (PPD) converters demonstrated a significantly lower incidence of allergic disease, and significantly lower serum IgE levels versus PPD negative school children (Shirakawa, T. et al., 1997, Science 275:77–9). Similar observations were made in an experimental murine system (Erb, K. I. et al., 1998, J. Exp. Med. 187:561–9). In this respect, exposure to MTB may be considered to pre-prime the host toward Th1 immunity. Moreover, a recent study demonstrated that the infection of dendritic cells with MTB resulted in the release of TNFα, and IL-12, as well as the up-regulation of MHC class I, ICAM-1, CD40, and B7 co-stimulatory molecules (Henderson, R. A. et al., 1997, J. Immunol. 159:635). This activation profile is very similar to the pattern induced with ISS. As ISS DNA was initially identified and isolated from MTB DNA, it is conceivable that this adjuvant plays a role in biasing the immune profile of MTB exposed hosts toward a Th1 phenotype, as do synthetic ISS-ODNs as demonstrated herein.

In gene vaccinated animals, ISS (CpG motifs) within the plasmid DNA (pDNA) backbone generate the necessary initial cytokine milieu (i.e., IL-12 and IFNs) to foster a Th1 response to the encoded antigen. Thus, gene vaccination plasmids provide both a source of adjuvant and antigen. These two activities are probably not simultaneous. The local induction of cytokine by ISS DNA is rapid (within 24 hours) and probably precedes the expression of sufficient amounts of antigen to elicit an effective immune response. A similar argument can be made for the up-regulation of co-stimulatory ligands. Thus, in gene vaccination, the pre-priming effects mediated by ISS DNA are likely to contribute to the Th1 biased immune response to the encoded antigen.

The above examples show that pre-priming enhances a variety of immune responses and is effective for enhancing both mucosal and systemic immunity. In summary, the invention provides a novel paradigm for Th1 biased immunization, called ISS pre-priming. Immunostimulatory sequence DNA administration biases the host immune system toward Th1 biased immune responses for up to 2 weeks. In addition, ISS delivered up to 7 days before antigen produces a stronger immune response than ISS/antigen co-immunization.

The data presented herein show that ISS can not only be used as an adjuvant in the traditional sense, but that it can also be used as an immuno-modifying therapeutic agent. For example, ISS might be i.d. injected or applied i.n. for the treatment of allergic rhinitis or inhaled to treat asthma. This immunologic strategy would provide relatively prolonged Th1 biased immunologic protection against continuous exposure to inhaled allergens. Instead of amplifying a pre-existing allergic Th2 biased immune response, allergen exposure would down-regulate allergic inflammation of the nasal mucosa and bronchial surface via the numerous type 1 cytokines released after ISS exposure. A similar approach might be effective for preventing or treating infectious diseases such as influenza or rotavirus gastroenteritis via a Th1 biased and activated immune system post ISS pre-priming. This invention provides ISS pre-priming as a new vaccination strategy, and a new paradigm for the prevention and treatment of infectious, allergic and malignant disease.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for enhancing an immune response to an antigenic substance, comprising administering intranasally a polynucleotide comprising an immunostimulatory nucleotide sequence (ISS) to a subject antigenic about one day to about seven days prior to exposure to the antigenic substance by the subject, wherein the ISS comprises the sequence 5'-rrcgyy-3' (SEQ ID NO: 1), 5'-rycgyy-3' (SEQ ID NO: 2), 5'-rrcgyycg-3' (SEQ ID NO: 3) or 5'-rycgyycg-3' (SEQ ID NO: 4), and wherein upon exposure to the antigenic substance, an immune response specific for the antigenic substance antigenic is enhanced relative to an immune response produced by administration of the substance alone.

2. A method of immunizing a subject against an antigenic substance, comprising administering intranasally to the subject a polynucleotide comprising an immunostimulatory nucleotide sequence (ISS) about one day to about seven days prior to exposing the subject to the antigenic substance, wherein the ISS comprises the sequence 5'-rrcgyy-3' (SEQ ID NO: 1), 5'-rycgyy-3' (SEQ ID NO: 2), 5'-rrcgyycg-3' (SEQ ID NO: 3) or 5'-rycgyycg-3' (SEQ ID NO: 4), and wherein upon exposure to the substance, an immune response specific for the antigenic substance is enhanced relative to an immune response produced by administration of the antigenic substance alone, and the subject is immunized against the antigenic substance.

3. A method of eliciting production of an antibody associated with a Th1 immune response, comprising administering intranasally to a subject a polynucleotide comprising an immunostimulatory nucleotide sequence (ISS) from about one day to about seven days prior to administration of an antigenic substance to the subject, wherein the ISS comprises the sequence 5'-rrcgyy-3' (SEQ ID NO: 1), 5'-rycgyy-3' (SEQ ID NO: 2), 5'-rrcgyycg-3' (SEQ ID NO: 3) or 5'-rrcgyycg-3' (SEQ ID NO: 4), and wherein upon exposure to the antigenic substance, production of antibody associated with a Th1 immune response specific for the antigenic substance is enhanced relative to an immune response produced by administration of the antigenic substance alone.

4. A method for modulating an immune response in a subject, the method comprising:

administering intranasally to a subject a polynucleotide comprising an immunostimulatory nucleotide sequence (ISS), wherein the ISS comprises the sequence 5'-rrcgyy-3' (SEQ ID NO: 1), 5'-rycgyy-3' (SEQ ID NO: 2), 5'-rycgyy-3' (SEQ ID NO: 3) or 5'-rycgyycg-3' (SEQ ID NO: 4), and wherein said polynucleotide is administered about one day to about seven days prior to exposure to an antigenic substance and in an amount effective to modulate an immune response specific for the antigenic substance in the subject upon exposure to the antigenic substance.

5. A method for modulating an immune response in a subject, the method comprising:

administering intradermally to a subject a polynucleotide comprising an immunostimulatory nucleotide sequence (ISS), wherein the ISS comprises the sequence 5'-rrcgyy-3' (SEQ ID NO: 1), 5'-rycgyy-3' (SEQ ID NO: 2), 5'-rrcgyycg-3' (SEQ ID NO: 3) or 5'-rycgyycg-3' (SEQ ID NO: 4), and wherein said polynucleotide is administered about three days to about 14 days prior to exposure to an antigenic substance and in an amount effective to modulate an immune response specific for the antigenic substance in the subject upon exposure to the antigenic substance.

6. A method for enhancing an immune response to an antigenic substance, comprising administering intradermally a polynucleotide comprising an immunostimulatory nucleotide sequence (ISS) to a subject said administering being about three days to about 14 days prior to exposure to the substance by the subject, wherein the ISS comprises the sequence 5'-rrcgyy-3' (SEQ ID NO: 1), 5'-rycgyy-3' (SEQ ID NO: 2), 5'-rrcgyycg-3' (SEQ ID NO: 3) or 5'-rycgyycg-3' (SEQ ID NO: 4), and wherein upon exposure to the substance, an immune response to the substance is enhanced relative to an immune response produced by administration of the substance alone.

7. A method of immunizing a subject against an antigenic substance, comprising administering intradermally to the subject a polynucleotide comprising an immunostimulatory nucleotide sequence (ISS), said administering being about three days to about 14 days prior to exposing the subject to the antigenic substance, wherein the ISS comprises the sequence 5'-rrcgyy-3' (SEQ ID NO: 1), 5'-rycgyy-3' (SEQ ID NO: 2), 5'-rrgyycg-3' (SEQ ID NO: 3) or 5'-rycgyycg-3' (SEQ ID NO: 4), and wherein upon exposure to the antigenic substance, an immune response specific for the antigenic substance is enhanced relative to an immune response produced by administration of the antigenic substance alone, and the subject is immunized against the antigenic substance.

8. A method of eliciting production of an antibody associated with a Th1 immune response, comprising administering intradermally to a subject a polynucleotide comprising an immunostimulatory nucleotide sequence (ISS), said administering being about three days to about 14 days prior to administration of an antigenic substance to the subject, wherein the ISS comprises the sequence 5'-rrcgyy-3' (SEQ ID NO: 1), 5'-rycgyy-3' (SEQ ID NO: 2), 5'-rrcgyycg-3' (SEQ ID NO: 3) or 5'-rycgyycg-3' (SEQ ID NO: 4), and wherein upon exposure to the antigenic substance, production of antibody associated with a Th1 immune response specific for the antigenic substance is enhanced relative to an immune response produced by administration of the antigenic substance alone.

9. The method of any one of claims 1–8, wherein the antigenic substance is an antigen of an infectious pathogen, an allergen or a cancer antigen.

10. The method of any one of claims 1–8, wherein the antigenic substance is an antigen of an infectious pathogen selected from the group consisting of a virus, a bacterium, a mycobacterium, and a parasite.

11. The method of any one of claims 1–8, wherein the polynucleotide comprises a backbone phosphate group modification.

12. The method of any one of claims 1–8, wherein the polynucleotide comprises a backbone phosphate group modification comprising a phosphorothioate or a phosphorodithioate.

13. The method of any one of claims 1–8, wherein the immune response is a Th1 response.

14. The method of any one of claims 1–8, wherein the polynucleotide is a plasmid.

* * * * *

SEQUENCE LISTING

<160> NUMBER OF SEQ ID NOS: 40

<210> SEQ ID NO 1
<211> LENGTH: 6
<212> TYPE: DNA
<213> ORGANISM: synthetic oligonucleotide

<400> SEQUENCE: 1 rrcgyy                                                                    6

<210> SEQ ID NO 2
<211> LENGTH: 6
<212> TYPE: DNA
<213> ORGANISM: synthetic oligonucleotide

<400> SEQUENCE: 2 rycgyy                                                                    6

<210> SEQ ID NO 3
<211> LENGTH: 8
<212> TYPE: DNA
<213> ORGANISM: synthetic oligonucleotide

<400> SEQUENCE: 3 rrcgyycg                                                                  8

<210> SEQ ID NO 4
<211> LENGTH: 8
<212> TYPE: DNA
<213> ORGANISM: synthetic oligonucleotide

<400> SEQUENCE: 4 rycgyycg                                                                  8

<210> SEQ ID NO 5
<211> LENGTH: 6
<212> TYPE: DNA
<213> ORGANISM: synthetic oligonucleotide

<400> SEQUENCE: 5 aacgtt                                                                    6

<210> SEQ ID NO 6
<211> LENGTH: 6
<212> TYPE: DNA
<213> ORGANISM: synthetic oligonucleotide

<400> SEQUENCE: 6 agcgtc                                                                    6

<210> SEQ ID NO 7
<211> LENGTH: 6
<212> TYPE: DNA
<213> ORGANISM: synthetic oligonucleotide

<400> SEQUENCE: 7 agcgtt                                                                    6

<210> SEQ ID NO 8
<211> LENGTH: 6
<212> TYPE: DNA
<213> ORGANISM: synthetic oligonucleotide

```
<400> SEQUENCE: 8 gacgtt                                                                    6

<210> SEQ ID NO 9
<211> LENGTH: 6
<212> TYPE: DNA
<213> ORGANISM: synthetic oligonucleotide

<400> SEQUENCE: 9 ggcgtt                                                                    6

<210> SEQ ID NO 10
<211> LENGTH: 6
<212> TYPE: DNA
<213> ORGANISM: synthetic oligonucleotide

<400> SEQUENCE: 10 aacgtc                                                                    6

<210> SEQ ID NO 11
<211> LENGTH: 6
<212> TYPE: DNA
<213> ORGANISM: synthetic oligonucleotide

<400> SEQUENCE: 11 agcgtc                                                                    6

<210> SEQ ID NO 12
<211> LENGTH: 6
<212> TYPE: DNA
<213> ORGANISM: synthetic oligonucleotide

<400> SEQUENCE: 12 gacgtc                                                                    6

<210> SEQ ID NO 13
<211> LENGTH: 6
<212> TYPE: DNA
<213> ORGANISM: synthetic oligonucleotide

<400> SEQUENCE: 13 ggcgtc                                                                    6

<210> SEQ ID NO 14
<211> LENGTH: 6
<212> TYPE: DNA
<213> ORGANISM: synthetic oligonucleotide

<400> SEQUENCE: 14 aacgcc                                                                    6

<210> SEQ ID NO 15
<211> LENGTH: 6
<212> TYPE: DNA
<213> ORGANISM: synthetic oligonucleotide

<400> SEQUENCE: 15 agcgcc                                                                    6

<210> SEQ ID NO 16
<211> LENGTH: 6
<212> TYPE: DNA
```

<213> ORGANISM: synthetic oligonucleotide

<400> SEQUENCE: 16 gacgcc                                                                6

<210> SEQ ID NO 17
<211> LENGTH: 6
<212> TYPE: DNA
<213> ORGANISM: synthetic oligonucleotide

<400> SEQUENCE: 17 ggcgcc                                                                6

<210> SEQ ID NO 18
<211> LENGTH: 6
<212> TYPE: DNA
<213> ORGANISM: synthetic oligonucleotide

<400> SEQUENCE: 18 agcgct                                                                6

<210> SEQ ID NO 19
<211> LENGTH: 6
<212> TYPE: DNA
<213> ORGANISM: synthetic oligonucleotide

<400> SEQUENCE: 19 gacgct                                                                6

<210> SEQ ID NO 20
<211> LENGTH: 6
<212> TYPE: DNA
<213> ORGANISM: synthetic oligonucleotide

<400> SEQUENCE: 20 ggcgct                                                                6

<210> SEQ ID NO 21
<211> LENGTH: 6
<212> TYPE: DNA
<213> ORGANISM: synthetic oligonucleotide

<400> SEQUENCE: 21 ttcgaa                                                                6

<210> SEQ ID NO 22
<211> LENGTH: 6
<212> TYPE: DNA
<213> ORGANISM: synthetic oligonucleotide

<400> SEQUENCE: 22 ggcgtt                                                                6

<210> SEQ ID NO 23
<211> LENGTH: 6
<212> TYPE: DNA
<213> ORGANISM: synthetic oligonucleotide

<400> SEQUENCE: 23 aacgcc                                                                6

<210> SEQ ID NO 24
<211> LENGTH: 6

```
<212> TYPE: DNA
<213> ORGANISM: synthetic oligonucleotide

<400> SEQUENCE: 24 gtcgtt                                                              6

<210> SEQ ID NO 25
<211> LENGTH: 8
<212> TYPE: DNA
<213> ORGANISM: synthetic oligonucleotide

<400> SEQUENCE: 25 agcgtccg                                                            8

<210> SEQ ID NO 26
<211> LENGTH: 8
<212> TYPE: DNA
<213> ORGANISM: synthetic oligonucleotide

<400> SEQUENCE: 26 aacgttcg                                                            8

<210> SEQ ID NO 27
<211> LENGTH: 8
<212> TYPE: DNA
<213> ORGANISM: synthetic oligonucleotide

<400> SEQUENCE: 27 agcgttcg                                                            8

<210> SEQ ID NO 28
<211> LENGTH: 8
<212> TYPE: DNA
<213> ORGANISM: synthetic oligonucleotide

<400> SEQUENCE: 28 gacgttcg                                                            8

<210> SEQ ID NO 29
<211> LENGTH: 8
<212> TYPE: DNA
<213> ORGANISM: synthetic oligonucleotide

<400> SEQUENCE: 29 ggcgttcg                                                            8

<210> SEQ ID NO 30
<211> LENGTH: 8
<212> TYPE: DNA
<213> ORGANISM: synthetic oligonucleotide

<400> SEQUENCE: 30 aacgttcg                                                            8

<210> SEQ ID NO 31
<211> LENGTH: 8
<212> TYPE: DNA
<213> ORGANISM: synthetic oligonucleotide

<400> SEQUENCE: 31 agcgtccg                                                            8

<210> SEQ ID NO 32
```

```
<211> LENGTH: 22
<212> TYPE: DNA
<213> ORGANISM: synthetic oligonucleotide

<400> SEQUENCE: 32
tgactgtgaa cgttcgagat ga                                          22

<210> SEQ ID NO 33
<211> LENGTH: 22
<212> TYPE: DNA
<213> ORGANISM: synthetic oligonucleotide

<400> SEQUENCE: 33
tgactgtgaa ccttagagat ga                                          22

<210> SEQ ID NO 34
<211> LENGTH: 9
<212> TYPE: PRT
<213> ORGANISM: e. coli

<400> SEQUENCE: 34

Thr Pro His Pro Ala Arg Ile Gly Leu
 1               5

<210> SEQ ID NO 35
<211> LENGTH: 21
<212> TYPE: DNA
<213> ORGANISM: synthetic oligonucleotide

<400> SEQUENCE: 35
gggacatcat caaaccagac c                                           21

<210> SEQ ID NO 36
<211> LENGTH: 21
<212> TYPE: DNA
<213> ORGANISM: synthetic oligonucleotide

<400> SEQUENCE: 36
gccaaccaag cagaagacag c                                           21

<210> SEQ ID NO 37
<211> LENGTH: 32
<212> TYPE: DNA
<213> ORGANISM: synthetic oligonucleotide

<400> SEQUENCE: 37
tgcatcttgg ctttgcagct cttcctcatg gc                               32

<210> SEQ ID NO 38
<211> LENGTH: 32
<212> TYPE: DNA
<213> ORGANISM: synthetic oligonucleotide

<400> SEQUENCE: 38
tggacctgtg ggttgttgac ctcaaacttg gc                               32

<210> SEQ ID NO 39
<211> LENGTH: 20
<212> TYPE: DNA
<213> ORGANISM: synthetic oligonucleotide

<400> SEQUENCE: 39
accacagtcc atgccatcac                                             20
```

-continued

```
<210> SEQ ID NO 40
<211> LENGTH: 20
<212> TYPE: DNA
<213> ORGANISM: synthetic oligonucleotide

<400> SEQUENCE: 40
tccaccaccc tgttgctgta                                              20
```